US006057275A

United States Patent [19]

Fair et al.

[11] Patent Number: 6,057,275

[45] Date of Patent: May 2, 2000

[54] BARS COMPRISING BENEFIT AGENT AND CATIONIC POLYMER

[75] Inventors: Michael Joseph Fair, Hackensack, N.J.; Michael Massaro, Congers, N.Y.; Harry Crookham, Lyndhurst; Gail Beth Rattinger, Teaneck, both of N.J.; James Joseph Dalton, Scottsdale, Ariz.; Terence James Farrell, West New York; Georgia Shafer, Rutherford, both of N.J.

[73] Assignee: Unilever Home & Personal Care USA, Division of Conopco, Inc., Greenwich, Conn.

[21] Appl. No.: 09/224,786

[22] Filed: Jan. 4, 1999

Related U.S. Application Data

[63] Continuation-in-part of application No. 09/140,312, Aug. 26, 1998, abandoned.

[51] Int. Cl.$^7$ .............................. A61K 7/50; C11D 17/00

[52] U.S. Cl. .......................... 510/151; 510/141; 510/152; 510/153; 510/155

[58] Field of Search .................................... 510/130, 141, 510/151, 152, 153, 155

[56] References Cited

U.S. PATENT DOCUMENTS

| | | |
|---|---|---|
| 3,761,418 | 9/1973 | Parran, Jr. . |
| 5,262,079 | 11/1993 | Kacher et al. . |
| 5,425,892 | 6/1995 | Taneri et al. . |
| 5,520,840 | 5/1996 | Massaro et al. . |
| 5,540,854 | 7/1996 | Fair et al. . |

FOREIGN PATENT DOCUMENTS

| | | |
|---|---|---|
| 95/26710 | 10/1995 | WIPO . |

*Primary Examiner*—Necholus Ogden
*Attorney, Agent, or Firm*—Ronald A. Koatz

[57] ABSTRACT

A bar composition in which use of specific ratio of cationic to surfactant has been found to remarkably enhance deposition of oil/emollient benefit agent.

12 Claims, 1 Drawing Sheet

BARS COMPRISING BENEFIT AGENT AND CATIONIC POLYMER

RELATED APPLICATIONS

The present application is a continuation-in-part of U.S. Ser. No. 09/140,312, filed Aug. 26, 1998 now abandoned.

FIELD OF THE INVENTION

The present invention relates to bar compositions capable of delivering benefit agents to the skin. More particularly the invention relates to bars containing relatively large amounts of hydrophilic structurant (ratio of hydrophilic to hydrophobic being at least 1:2, preferably greater than 40:60, more preferably at least 1:1 and most preferably above 1:1) and in which cationic polymer, particularly cationic polymer having minimum level of charge density, has been found to unexpectedly enhance deposition of benefit agent in such bars.

BACKGROUND OF THE INVENTION

Cationic polymers are well known in the art. For example in liquid cleansers, cationic hydrophilic polymers such as Polymer JR® from Americhol or Jaguar® from Rhone Poulenc have been used to enhance delivery of benefit agents (EP 93,602; WO 94/03152; and WO 94/03151).

Cationic polymers have also been used in bar formulations. U.S. Pat. No. 3,761,418 to Parran, Jr., for example, teaches detergent composition (including bar soaps) containing water insoluble particulate substances such as antimicrobial agents and certain cationic polymers to enhance deposition and retention of such particulate substances. Although bar soap formulations are used in the examples, all of the formulations are primarily structured with soap and/or fatty acid. Further, not only are benefit agents (oils/emollients) not disclosed, but it would be expected that hydrophobic structurants would interfere with deposition of any such oils/emollients.

WO No. 95/26710 to Kacher et al. (assigned to P&G) teaches skin moisturizing and cleansing bar containing skin cleansing agent and lipid moisturizing agent. A preferred optional ingredient is one or more cationic polymeric skin conditioning agent added to provide a tactile cue. Again, however, the bar is made of a rigid crystalline network structure consisting essentially of selected fatty acid soap material. Applicants have found such fatty acid soap material to be detrimental to deposition.

U.S. Pat. No. 5,425,892 to Taneri et al. teach personal cleansing freezer bars comprising a skeleton structure of neutralized carboxylic acid soap. The patent teaches polymeric skin feel aids, water soluble organics and oils. However the bars, as noted, have a distinctive carboxylic acid structure differing from bars of the invention containing relatively large amounts of hydrophilic structurant.

Hydrophilic structured bars themselves are also taught, for example, in U.S. Pat. No. 5,520,840 to Massaro et al. or U.S. Pat. No. 5,540,854 to Fair et al. There is no teaching in these references, however, of cationic polymers and no suggestion that such cationics could enhance deposition of oil/emollients in bars containing relatively large amounts of hydrophilic structurant. Further there is no teaching or suggestion in this or any other reference of a critical cationic to surfactant ratio above which deposition of oils/emollients is significantly enhanced or that cationics must have minimum level of charge density.

Finally, U.S. Pat. No. 5,262,079 to Kacher et al. teaches firm, mild neutral pH cleansing bars comprising 5–50% by wt. monocarboxylic fatty acids (which provides skeletal structure), 20 to 65% bar firmness aid and 15% to 55% water. The bars may contain optional polyols (0–40%) as "bar firmness aids". The bars are primarily fatty acid structured and the only bar firmness aids exemplified are isethionate (i.e., they do not have minimum levels of hydrophilic to hydrophobic structurant). Further, cationics disclosed are guar, quaternized guar etc., all of which have charge density below 0.007. There is thus no recognition that only cationic polymers having minimum charge activity are adequate for purpose of the invention.

BRIEF SUMMARY OF THE INVENTION

Suddenly and unexpectedly applicants have discovered that cationics, i.e., cationic polymer of minimum charge density level, can be used to enhance deposition of oils/emollients in bars comprising relatively large amount of hydrophilic structurant (e.g., ratio of hydrophilic of hydrophobic structurant being at least 1:2, preferably greater than 40:60, more preferably at least 1:1 and most preferably above 1:1; further total soap and hydrophobic structurant should exceed hydrophilic structurant by no more than 10% by weight total composition) and further that there is a minimum critical ratio of cationic polymer to surfactant at which deposition is remarkably enhanced. In addition, it is critical that levels of surfactant, particularly anionic, not exceed certain range (lest deposition be affected) and that minimum amounts of oil/emollient be used.

More specifically, the subject invention relates to bar compositions comprising:

(a) 10 to 50%, preferably 20% to 40% by wt. of a synthetic, non-soap surfactant, preferably an anionic surfactant (e.g., acyl isethionate or alkali metal lauryl ether sulfate);

(b) 10 to 40%, preferably 15 to 35% by wt. of a hydrophilic structurant having a melting point in the range 40° to 100° C. (such structurant will generally have solubility of at least 10% at room temperature);

(c) 5 to 20% of a water insoluble structurant with MP in range 40° C. to 200° C.;

(d) 2% to 40%, preferably 5% to 20% benefit agent; and (e) 1.0% to 10% cationic polymer;

wherein the amount of insoluble structurant (c) and soap, if any, present exceeds the amount of hydrophilic structurant (b) by no more than 10% by wt. total bar composition;

wherein the amount of cationic polymer (e) is such that ratio of cationic to surfactant is 0.06 to 1 to 1:1, more preferably 0.08:1 to 0.5:1;

and wherein charge density of cationic polymer (number of monovalent charges per repeat unit divided by molar mass of repeat unit) is greater than 0.007.

DETAILED DESCRIPTION OF THE INVENTION

Figure 1:
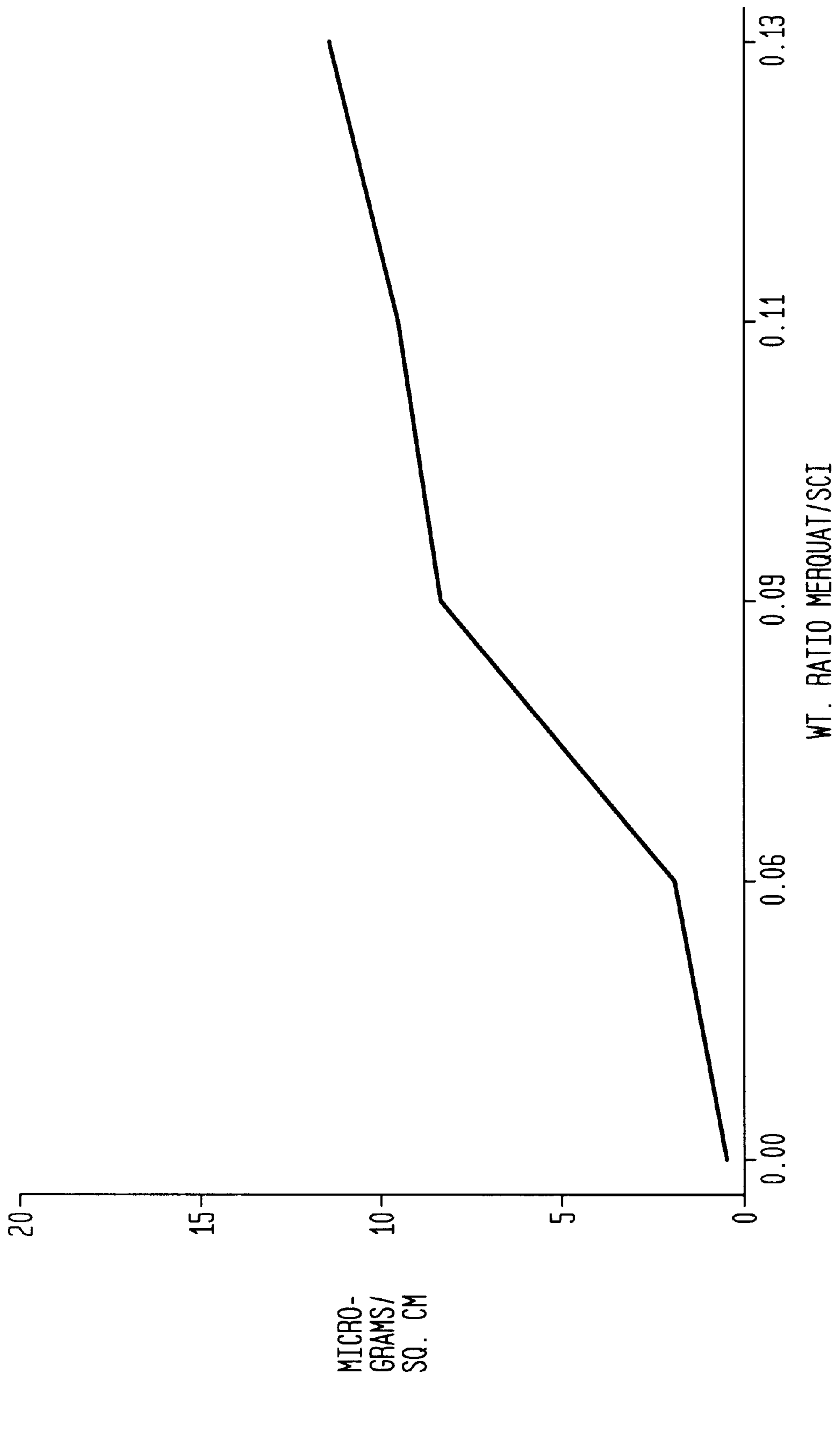
FIG. 1 shows deposition results depending on ratio of cationic to surfactant. As seen, only when ratio of cationic to surfactant reaches certain minimum level does deposition significantly increase.

The present invention relates to relatively low active bars (e.g., 50% active, preferably less than 40%, more preferably 30% and less active) wherein there is present a relatively large amount of hydrophilic structurant (hydrophobic structurant and soap, if present, should comprise no more than about 10% by wt. more than amount of hydrophilic structurant) and which further comprises relatively large amount of oil/emollient (i.e., at least 2%). Unexpectedly applicants have discovered that when the ratio of cationic to surfactant in such bars is equal to or above certain defined ratio, the deposition of benefit agent from the bar is remarkably enhanced. The cationic polymers used must also have minimum defined levels of charge density.

The bar is described in greater detail below.

The bars of the inventions should contain from about 10% to 50% by wt. more preferably 15 to 40% of a synthetic, non-soap surfactant. Suitable surfactants are generally selected from the group consisting of anionic, nonionic, amphoteric, zwitterionic and/or cationic surfactants and mixtures thereof such as are well known in the art.

More specifically, the surfactant system will generally comprise at least one anionic surfactant, a zwitterionic surfactant or, preferably mixtures of anionic or anionics and zwitterionic surfactant.

The anionic surfactant which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium laurel ether sulfates are preferred.

The anionic may also be alkyl sulfosuccinates (including mono and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$R^1O_2CCH_2CH(SO_3M)CO_2M$; and amide-MEA sulfosuccinates of the formula $$R^1CONHCH_2CH_2O_2CCH_2CH(SO_3M)CO_2M$$

wherein $R^1$ ranges from $C_8$–$C_{22}$ alkyl and M is a solubilizing cation.

Sarcosinates are generally indicated by the formula $RCON(CH_3)CH_2CO_2M$, wherein R ranges from $C_8$–$C_{20}$ alkyl and M is a solubilizing cation.

Taurates are generally identified by formula $$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 50% by weight of the total bar composition. Preferably, this component is present from about 20% to about 40%.

The acyl isethionate may be an alkoxylated isethionate such as is described in llardi et al., U.S. Pat. No. 5,393,466, hereby incorporated by reference.

Anionic surfactant may also be a "soap". By soap is meant alkali metal salts of aliphatic alkane- or alkene monocarboxylic acids, more generally known as $C_{12}$–$C_{22}$ alkyl fatty acids. Sodium and potassium salts are preferable. A preferred soap is a mixture of about 15% to about 45% coconut oil and about 55% to about 85% tallow.

The soaps may contain unsaturation in accordance with commercially acceptable standards. Excessive unsaturation is normally avoided.

In general the anionic component will comprise from about 10% to 50% of the bar composition.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

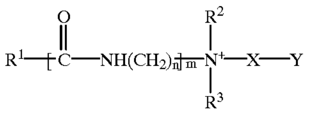

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

x is alkylene of 1 to 3 carbon atoms optionally substituted with hydroxyl, and y is $—CO_2—$ or $—SO_3—$ Suitable amphoteric detergents within the above general formula include simple betaines of formula:

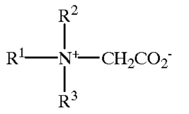

and amido betaines of formula:

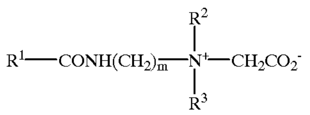

where m is 2 or 3.

In both formulae $R^1$ is alkyl or alkenyl of 7 to 18 carbons; and $R^2$ and $R^3$ are independently alkyl, hydroxyalkyl or carboxylalkyl of 1 to 3 carbons. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

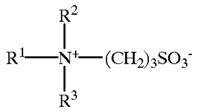

or

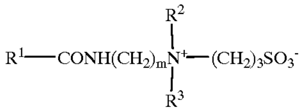

where m is 2 or 3, or variants of these in which $—(CH_2)_3SO_3^-$ is replaced by

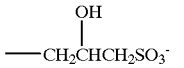

In these formulae $R^1$, $R^2$ and $R^3$ are as discussed for the amido betaine.

Amphoteric generally comprises 1% to 10% of the bar composition.

Other surfactants (i.e., nonionics, cationics) may also be optionally used although these generally would not comprise more than 0.01 to 20% by wt. of the bar composition.

Nonionic surfactants include in particular the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference and polyhydroxyamides such as described in U.S. Pat. No. 5,312,954 to Letton et al., hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Volume I & II) by Schwartz, Perry & Berch, both of which are also incorporated into the subject application by reference.

A preferred composition comprises 10 to 50% acyl isethionate and 1% to 10% betaine.

Hydrophilic Structurant

Another critical compound of the bar is hydrophilic structurant (e.g., polyalkylene glycol).

This component should comprise greater than 10% by wt. to 40%, preferably greater than 15% to 35% by wt. of the bar composition.

The structurant has a melting point of 40° to 100° C., preferably 45° C. to 100° C., more preferably 50° to 90° C. Generally these structurants will be at least 10% water soluble at room temperature.

Materials which are envisaged as the water soluble structurant (b) are moderately high molecular weight polyalkylene oxides of appropriate melting point and in particular polyethylene glycols or mixtures thereof.

Polyethylene glycols (PEG's) which may be used may have a molecular weight in the range 1,500–20,000.

It should be understood that each product (e.g., Union Carbide's Carbowax® PEG-8,000) represents a distribution of molecular weights. Thus PEG 8,000, for example, has an average MW range of 7,000–9,000, while PEG 300 has an average MW range from 285 to 315. The average MW of the product can be anywhere between the low and high value, and there may still be a good portion of the material with MW below the low value and above the high value.

In some embodiments of this invention it is preferred to include a fairly small quantity of polyalkylene glycol (e.g., polyethylene glycol) with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a larger quantity of other water soluble structurant (b) such as the above mentioned polyethylene glycol of molecular weight 1,500 to 10,000.

Some polyethylene oxide polypropylene oxide block copolymers melt at temperatures in the required range of 40 to 100° C. and may be used as part or all of the water soluble structurant (b). Preferred here are block copolymers in which polyethylene oxide provides at least 40% by weight of the block copolymer. Such block copolymers may be used, in mixtures with polyethylene glycol or other polyethylene glycol water soluble structurant.

In addition, there may be a mixture of lower and higher MW polyalkylene glycols as described in U.S. Pat. No. 5,683,973 to Post et al., hereby incorporated by reference into the subject application.

It should be noted that, although they may not necessarily be used by themselves, certain water soluble adjuvant fillers may be used in combination with the water soluble structurant. Among these, for example, are included maltodextrin and similar water soluble starches. If included, these adjuvants would comprise no more than about 10% by wt. of the composition.

Water Insoluble Structurant

The water insoluble structurants are also required to have a melting point in the range 40–100° C., more preferably at least 50° C., notably 50° C. to 90° C. Suitable materials which are particularly envisaged are fatty acids, particularly those having a carbon chain of 12 to 24 carbon atoms. Examples are lauric, myristic, palmitic, stearic, arachidonic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkanols of 8 to 20 carbon atoms, particularly cetyl alcohol. These materials generally have a water solubility of less than 5 g/liter at 20° C.

The relative proportions of the water soluble structurants and water insoluble structurants govern the rate at which the bar wears during use. The presence of the water insoluble structurant tends to delay dissolution of the bar when exposed to water during use and hence retard the rate of wear.

In general, insoluble structurant will comprise 5 to 20% by wt. of the composition.

According to the invention, the amount of water insoluble structurant (c) should not exceed the amount of hydrophilic structurant (b) plus any soap which may be present by more than about 10% by wt. While not wishing to be bound by theory, this is believed to be so because when there is too much soap and/or hydrophilic structurant, level of deposition is reduced.

Benefit Agent

The benefit agent of the compositions of the invention is included in the compositions to moisturize, condition and/or protect the skin. By "benefit agent" is meant a substance that softens the skin (stratum corneum) and keeps it soft by retarding the decrease of its water content and/or protects the skin.

Preferred benefit agents include:

(a) silicone oils, gums and modifications thereof such as linear and cyclic polydimethylsiloxanes, amino, alkyl alkylaryl and aryl silicone oils;

(b) fats and oils including natural fats and oils such as jojoba, soybean, sunflower, rice bran, avocado, almond, olive, sesame, persic, castor, coconut, mink oils; cacao fat, beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petroleum jelly, microcrystalline wax, ceresin, squalene, squalane, and mineral oil;

(f) higher fatty acids such as lauric, myristic, palmitic, stearic, behenic, oleic, linoleic linolenic, lanolic, isostearic and poly unsaturated fatty acids (PUFA) acids;

(g) higher alcohols such as lauryl, cetyl, steryl, oleyl, behenyl, cholesterol and 2-hexadecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate (for example lauryl lactate), alkyl citrate and alkyl tartrate;

(i) essential oils such as fish oils, mentha, jasmine, camphor, white cedar, bitter orange peel, ryu, turpentine, cinnamon, bergamont, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, pinene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids;

(n) humectants such as glycerin, propylene glycol and sorbitol; and (o) mixtures of any of the foregoing components.

Where adverse interactions between the benefit agent and surface active are likely to be particularly acute, the benefit agent may be incorporated in the compositions of the invention in a carrier.

Such benefit agents include lipids; alkyl lactates; sunscreens; esters such as isopropyl palmitate and isopropyl myristate; and vitamins. The carrier can, for example, be a silicone or hydrocarbon oil which is not solubilized/micellized by the surface active phase and in which the benefit agent is relatively soluble.

Particularly preferred benefit agents include silicone oils, gums and modification thereof, esters such as isopropyl palmitate and myristate and alkyl lactates, and vegetable oils such as sunflower seed oil.

The benefit agent can be provided in the form of an emulsion.

The benefit agent of the invention may also function as a carrier to deliver efficacy agents to skin treated with the compositions of the invention. This route is particularly useful for delivering efficacy agents which are difficult to deposit onto the skin or those which suffer detrimental interactions with other components in the composition. In such cases the carrier is as often a silicone or hydrocarbon oil which is not solubilized/micellized by the surface active phase and in which the efficacy agent is relatively soluble. Examples of such efficacy agents include anti-viral agents; hydroxycaprylic acids; pyrrolidone; carboxylic acids; 3,4,4'-trichlorocarbanilide; benzoyl peroxide; perfumes; essential oils; germicides and insect repellents such as 2,4,4'-trichloro-2'-hydroxydiphenyl ether (Irgasan DP300); salicylic acid; willow extract, N,N-dimethyl m-toluamide (DEET); and mixtures thereof.

The benefit agent comprises 2 to 40%, preferably 5 to 20% by wt. of the composition.

Finally, the cationic polymer (deposition aid) is a water soluble cationic polymer or copolymers having a molecular weight from about 1,000 to 2,000,000 and a high cationic charge density. Specifically, the cationic charge density should be at least 0.007 and higher where cationic charge density is defined as number of monovalent charges per repeat unit divided by the molar mass of repeat unit. Thus, for example, a Jaguar® type cationic such as Jaguar C14S® (such as used in example RR of Kacher et al. U.S. Pat. No. 5,262,079) has charge density of 0.0008, below the threshold of invention as does [N-[-3-(dimethylammonio) propyl] urea dichloride (Mirapol A15®) which has charge density of 0.00661. By contrast, dimethyldiallylammonium chloride (Mirquat 100®) has density of 0.00793 and is within the invention.

It is also important for the cationic polymer to be (a) fully hydrated prior to incorporation in the bar formulation and (b) at a concentration of 1% by wt. or higher for the desired benefit, i.e., enhanced deposition. The commercial application (usefulness) of the said invention would therefore require the cationic polymer to be at a relatively high concentration when hydrated to avoid the impracticality, difficulty and high costs of drying the syndet bar formulation. A cationic polymer such as dimethyidiallylammonium chloride (Tradename Mirquat 100) can be prepared at concentrations of 40% (60% water), whereas the low charge density quaternized guar cationic polymer (Tradename Jaguar C14S) exemplified by Kacher et al. can only be prepared at concentrations of approximately 3% (97% water) and are not practical on a commercial scale.

Exemplary cationic polymers which may be used according to the invention include Salcare® type polymers from Allied Colloids, and Merquat® type polymers from Calgon.

Those cationic polymers which are generally not applicable to the invention are the high molecular weight, low charge density polymers such as Polymer JR-400® from Amerchol and cationic polysaccharides of the cationic guar gum class such as Jaguar C14S® from Rhone-Poulenc.

It is an important aspect of the invention that there be a minimum amount of cationic polymer be used. Preferably, ratio of cationic to surfactant is 0.06:1 to 1:1, more preferably 0.08 to 1 to 0.5 to 1.

In addition ratio of hydrophilic structurant to total of soap and hydrophobic structurant should be at least 1:2, preferably 40:60, more preferably at least 1:1 and most preferably greater than 1:1.

Except in the operating and comparative examples, or where otherwise explicitly indicated, all numbers in this description indicating amounts or ratios of material or conditions of reaction, physical properties of materials and/or use are to be understood as modified by the word "about".

Further, when used in the specification and claims, the term comprises or comprising is to be understood to specify the presence of stated features integers, steps, components etc., but not to preclude the presence or addition of one or more features, integers, steps, components or groups thereof.

The following examples are intended to further illustrate the invention and are not intended to limit the claims in any way.

EXAMPLES

Materials and Methods

Materials

Sodium cocoyl isethionate was supplied by Lever Baltimore, Polyethylene glycol (PEG 8000) was supplied by Union Carbide, and Merquat 100 (cationic polymer) was supplied by Calgon Corporation. Polydimethylsiloxane (PDMS) with viscosity of 60,000 cs was from Dow Corning, Maltodextrin was from Grain Processing Corp., and the cocoamidopropyl betaine was from Goldschmidt Palmitic, stearic acid, and sodium stearate were supplied by Unichema.

In-Vivo Deposition Measurements

Attenuated Total Reflectance Fourier Transform Infrared Spectroscopy (ATR-FTIR) was the analytical technique used to measure silicone deposition. The standard procedure is documented below.

Formulation Processing

Bar formulations were prepared in a 2-liter Patterson mixer. The fatty acid and sodium stearate were mixed together at 90° C. Cocoyl isethionate was then added followed by the betaine and minor ingredients. After mixing for thirty minutes and drying to approximately 7% water, a polyethylene glycol and maltodextrin was added. This was mixed for an additional ten minutes. The cover was removed and the silicone and Mirquat 100 were added. The moisture content was determined by Karl Fisher titration with a turbo titrator. At the final moisture level (~5%), the formulation was dropped onto a heated applicator roll and then was chipped over a chill roll. The chill roll chips were plodded in a Weber Seelander duplex refiner with screw speed at ~20 rpm. The nose cone of the plodder was heated to 45–50° C. The cut billets were stamped using a Weber Seelander L4 hydraulic press with a nylon, pillow-shaped die in place.

The incorporation of benefit agent (e.g., polydimethylsiloxane) into Dove®-like compositions (e.g., high acyl isethionate bars structured with fatty acid) or primarily soap based compositions results in negligible deposition of the benefit agent. High surfactant levels (e.g., 60%) and insoluble structurants (e.g., fatty acid), generally inhibit transfer of benefit agent onto the skin. Even addition into lower active, hydrophilic structured bars such as those taught in U.S. Pat. No. 5,520,840 to Massaro et al. result in little deposition. In order to study effect of cationic polymer in such low active, hydrophilic structurant bars, however, the following compositions were prepared.

TABLE 1

| Component | Ex. 1 | Ex. 2 | Ex. 3 | Ex. 4 | Ex. 5 |
|---|---|---|---|---|---|
| Na cocoyl isethionate | 18.75 | 22.5 | 26.25 | 30.0 | 30.0 |
| PEG 8000 | 25.75 | 21.0 | 16.25 | 15.5 | 11.5 |
| Merquat 100 | 1.0 | 2.0 | 3.0 | 0 | 4.0 |
| PDMS (Polydimethylsiloxane) | 10.0 | 10.0 | 10.0 | 10.0 | 10.0 |
| Palmitic-Stearic Acid | 14.0 | 14.0 | 14.0 | 14.0 | 14.0 |
| Maltodextrin | 8.0 | 8.0 | 8.0 | 8.0 | 8.0 |
| Na Stearate | 5.0 | 5.0 | 5.0 | 5.0 | 5.0 |
| CAP Betaine | 5.0 | 5.0 | 5.0 | 5.0 | 5.0 |
| Na Isethionate | 2.2 | 2.2 | 2.2 | 2.2 | 2.2 |
| Target Water | 4.0 | 4.0 | 4.0 | 4.0 | 4.0 |
| PEG 540 | 5.0 | 5.0 | 5.0 | 5.0 | 5.0 |
| Coconut Fatty Acid | 1.1 | 1.1 | 1.1 | 1.1 | 1.1 |

In general, compositions were prepared by mixing ingredients at temperature sufficiently high to provide mix, cooling on chill roll to form chips/flakes, extruding, cutting and stamping. Compositions made are set forth in Table 1 above.

Attenuated Total Reflectance Fourier Transform Infrared Spectroscopy (ATR-FTI) was the analytical technique used to measure silicone deposition. In the standard procedure, the test bar is wetted and rotated ten times in the hand, the inner forearm is then wetted and the bar is rubbed ten times on the forearm. This is followed by a thirty second wash and a fifteen second rinse. The arm is then dried and an infrared scan of the inner forearm is obtained. The silicone is quantified by integrating the absorption band between 770 $cm^{-1}$ and 835 $cm^{-1}$. This is plotted on a standard curve and the deposition value in $\mu g/cm^2$ is reported.

The deposition results of the experimental design formulations are summarized in Table 2 and depicted graphically in FIG. 1. The wide variance observed is due to different skin types and skin conditions, requiring a minimum of approximately 8 independent measurements per prototype.

TABLE 2

In-Vivo Deposition of Experimental Design Bars

| Example # | SCI | Merquat | Deposition $\mu$g/cm2 | Std. Dev. | N | Wt. Ratio of Merquat/SCI |
|---|---|---|---|---|---|---|
| Ex. 4 | 30.0 | 0.0 | 0.4 | 0.8 | 9 | |
| Ex. 1 | 18.75 | 1.0 | 1.5 | 0.9 | 8 | 0.053 |
| Ex. 2 | 22.5 | 2.0 | 7.8 | 8.5 | 16 | 0.089 |
| Ex. 3 | 26.25 | 3.0 | 9.4 | 7.4 | 17 | 0.114 |
| Ex. 5 | 30.0 | 4.0 | 11.3 | 9.3 | 19 | 0.133 |

As seen, the amount of oil deposited on the skin appears to be a function of the cationic polymer to surfactant ratio. Specifically, a minimum ratio of 0.06 seems to be required. In the absence of polymer, virtually no silicone is detected on the skin from the bar prototypes. When the polymer:surfactant ratio is increased, a considerable increase in deposition is observed.

The following formulations were selected for further deposition.

| Component: | Ex. 6 | Ex. 7 | Ex. 8 (Body Wash) |
|---|---|---|---|
| Na Cocoyl Isethionate | 30.0 | 40.0 | 6.5 |
| PEG 8000 | 13.0 | 10.0 | 0 |
| PEG 540 | 5.0 | 5.0 | 0 |
| Cationic Polymer | 2.5 | 2.5 | 0.55 |
| Polydimethyl Siloxane | 10.0 | 10.5 | 5.0 |
| Palmitic-Stearic Acid | 14.0 | 14.0 | 0 |
| Na Laureth Sulfate | 0 | 0 | 6.5 |
| CAP Betaine | 5.0 | 5.0 | 5.6 |
| Lauro Amphoacetate | 0 | 0 | 5.6 |
| Isostearic Acid | 0 | 0 | 5.0 |
| Maltodextrin | 8.0 | 5.0 | 0 |
| Na Stearate | 5.0 | 5.0 | 0 |
| Na Isethionate | 2.2 | 2.2 | 0 |
| Water | 4.0 | 4.0 | qa. 100 |

For Example 6, ratio cationic/surfactant = 0.083
For Example 7, ratio cationic/surfactant = 0.0625

Example 6 contained 30% sodium cocoyl isethionate (SCI) with 2.5% Merquat and 10% PDMS. In Example, the SCl was increased to 40%. The Merquat and PDMS levels were not changed.

The deposition results from the formulations are depicted in Table 4 below:

TABLE 4

| Experiment # | Deposition μg/cm2 |
|---|---|
| Ex. 6 | 14.5 +/− 10.3 |
| Ex. 7 | 17.2 +/− 95 |
| Ex. 8 | 0.8 +/− 1.3 |

Table 4 also compares in-vivo deposition from the bar prototypes (Examples 6 & 7) to a liquid body wash (Example 8). As noted, significantly higher levels of oil are deposited on the skin from the bar prototypes.

We claim:

1. A bar composition comprising:

(a) 10% to 50% by wt. synthetic non-soap surfactant selected from the group consisting of anionic, nonionic, cationic, amphoteric/zwitterionic surfactants and mixtures thereof;

(b) 10% to 40% by wt. of a hydrophilic structurant having a melting range 40° to 100° C.;

(c) 5% to 20% by wt. of a water insoluble structurant with MP 40° to 200° C.;

(d) 2% to 40% benefit agent;

(e) 1.0% to 10% by wt. cationic polymer which is an alkali metal salt of a dialkyl diallyl ammonium;

wherein the amount of insoluble structurant (c) and soap; if any, exceeds amount of hydrophilic structurant (b) by no more than 10% by wt. of total bar composition; and wherein the amount of cationic polymer (e) is such that ratio of cationic polymer to surfactant is 0.06:1 to 1:1; and wherein charge density of cationic polymer is greater than 0.007.

2. A composition according to claim 1, wherein surfactant is an anionic surfactant.

3. A composition according to claim 2, wherein surfactant is acyl isethionate or alkali metal alkyl ether sulfate.

4. A composition according to claim 1, comprising 15 to 40% by wt. (a).

5. A composition according to claim 1, comprising 15 to 35% by wt. (b).

6. A composition according to claim 1, wherein hydrophilic structurant (b) is at least 10% water soluble at room temperature.

7. A composition according to claim 1, wherein hydrophilic structurant (b) is selected from the group consisting of polyalkylene oxides having MW 1500 to 20,000 and block copolymers of polyethylene and polypropylene oxide.

8. A composition according to claim 1, wherein insoluble structurant (c) is $C_{12}$ to $C_{24}$ fatty acid.

9. A composition according to claim 1, wherein benefit agent (d) comprises 5 to 20% by wt. benefit agent.

10. A composition according to claim 1, wherein cationic polymer is a cationic polymer or copolymer having molecular weight about 1,000 to 2,000,000 and cationic charge density greater than 0.001.

11. A composition according to claim 1, comprising 1.0% to 7% cationic polymer.

12. A composition according to claim 1, wherein ratio of cationic to surfactant is 0.08:1 to 0.5 to 1.

* * * * *